United States Patent
Harding et al.

(10) Patent No.: US 7,176,172 B2
(45) Date of Patent: *Feb. 13, 2007

(54) QUATERNARY AMMONIUM POLYOL SALTS AS ANTI-AGING ACTIVES IN PERSONAL CARE COMPOSITIONS

(75) Inventors: Clive Roderick Harding, Tenafly, NJ (US); Bijan Harichian, Warren, NJ (US)

(73) Assignee: Unilever Home & Personal Care USA, Division of Conopco, Inc., Greenwich, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 10/992,405

(22) Filed: Nov. 18, 2004

(65) Prior Publication Data

US 2006/0089277 A1    Apr. 27, 2006

Related U.S. Application Data

(63) Continuation-in-part of application No. 10/972,483, filed on Oct. 25, 2004, and a continuation-in-part of application No. 10/973,023, filed on Oct. 25, 2004, now Pat. No. 7,087,560, and a continuation-in-part of application No. 10/972,590, filed on Oct. 25, 2004.

(51) Int. Cl.
    *C11D 1/62* (2006.01)
(52) U.S. Cl. ............ 510/130; 510/119; 510/123; 510/504
(58) Field of Classification Search ........... 510/130, 510/119, 123, 504
    See application file for complete search history.

(56) References Cited

U.S. PATENT DOCUMENTS

| | | |
|---|---|---|
| 3,558,501 A | 1/1971 | McGuire et al. |
| 4,663,159 A | 5/1987 | Brode, II et al. |
| 4,689,217 A | 8/1987 | Restaino et al. |
| 4,690,817 A | 9/1987 | Davis et al. |
| 4,775,715 A | 10/1988 | Beresniewicz et al. |
| 5,091,171 A | 2/1992 | Yu et al. |
| 5,698,183 A | 12/1997 | Langer et al. |
| 6,265,364 B1 | 7/2001 | Kilpatrick-Liverman et al. |
| 6,290,978 B2 | 9/2001 | Mak et al. |
| 6,649,177 B2 | 11/2003 | Howard et al. |
| 2003/0095990 A1 | 5/2003 | Hua et al. |
| 2003/0206933 A1 | 11/2003 | Wiesche et al. |
| 2003/0211952 A1 | 11/2003 | Erazo-Majewicz et al. |
| 2004/0156877 A1 | 8/2004 | Tokuyama et al. |

FOREIGN PATENT DOCUMENTS

| | | |
|---|---|---|
| EP | 1 179 339 | 2/2002 |
| EP | 1 366 742 | 12/2003 |
| JP | 63068514 | 3/1988 |
| JP | 1249709 | 10/1989 |
| JP | 9012589 | 1/1997 |
| WO | 90/03161 | 4/1990 |
| WO | 96/35410 | * 11/1996 |
| WO | 00/61066 | 10/2000 |

OTHER PUBLICATIONS

International Search Report.
Martin M. Rieger: "Harry's Cosmeticology" 2000, chemical Publishing Co., Inc. NY, XP002363783, pp. 377-378.
Written Opinion.
Dow—Quat 188 Cationic Monomer: Overview, Jun. 30, 2004.
Arch Personal Care Products Brochure—Honeyquat 50 Substantive Honey Derivative, Jan. 2004.
Arch Personal Care Products—*In vivo* study of moisturizing effects of HoneyQuat 50, Jan. 2004.

* cited by examiner

*Primary Examiner*—Charles Boyer
(74) *Attorney, Agent, or Firm*—Milton L. Honig

(57) ABSTRACT

A personal care product is provided which includes a package filed with a personal care composition and instructions printed on or associated with the package indicating topical use of the composition on skin for purposes of controlling the signs of aging. The composition includes a quaternary ammonium compound selected from (a) salts of hydroxypropyltri($C_1$–$C_3$ alkyl)ammonium mono-substituted mono-saccharide; (b) salts of hydroxypropyltri($C_1$–$C_3$ alkyl) ammonium mono-substituted polyols, the salts having a cation of an average molecular weight no higher than about 450 and the salt having a $T_g$ no higher than about 10° C.; (c) dihydroxypropyltri($C_1$–$C_3$ alkyl)ammonium salts; (d) chlorohydroxypropyltri($C_1$–$C_3$ alkyl)ammonium salts; and (e) mixtures thereof.

7 Claims, No Drawings

QUATERNARY AMMONIUM POLYOL SALTS AS ANTI-AGING ACTIVES IN PERSONAL CARE COMPOSITIONS

CROSS REFERENCES

This application claims the benefit of priority from U.S. application Ser. No. 10/972,483 filed Oct. 25, 2004; Ser. No. 10/973,023 filed Oct. 25, 2004 now U.S. Pat. No. 7,087,560; and Ser. No. 10/972,590 filed Oct. 25, 2004 currently pending.

BACKGROUND OF THE INVENTION

1. Field of the Invention

The invention concerns quaternary ammonium salts of polyols in personal care compositions for purposes of delaying onset and treating the signs of aging.

2. The Related Art

Forever young. Adults as they age seek to preserve the indicia of youth. Through the ages cosmetics have proved valuable for retarding the signs of the aging process. Facial foundations, creams and lotions have all helped in the cover up. Yet few really effective actives are available in the cosmetic chemist's arsenal.

Two classes of materials have been clinically proven as providing some relief from the signs of aging. Alpha-hydroxycarboxylic acid derivatives are used widely in cosmetic commerce. Illustrative is U.S. Pat. No. 5,091,171 (Yu et al.). Retinol (Vitamin A) is an endogenous compound which occurs naturally in the human body. This material and its derivatives have been used extensively in the treatment of a variety of skin disorders and as repair or renewal agents.

Both alpha-hydroxycarboxylic acids and retinol as well as many of their derivatives tend to produce stinging sensation and even redness on the skin when present at levels sufficient to be effective. Consumers would of course prefer performance without side effects.

Accordingly, there still remains a need for materials which can be effective against the signs of aging and that yet have no adverse side effects.

SUMMARY OF THE INVENTION

A personal care product is provided which includes:
(A) a package filled with a personal care composition which includes:
  (i) from about 0.1 to about 30% by weight of a quaternary ammonium compound selected from the group consisting of:
    (a) salts of hydroxypropyltri($C_1$–$C_3$ alkyl)ammonium mono-substituted mono-saccharide;
    (b) salts of hydroxypropyltri($C_1$–$C_3$ alkyl)ammonium mono-substituted polyols, the salt having a cation of an average molecular weight no higher than about 450 and the salt having a $T_g$ no higher than about 10° C.;
    (c) dihydroxypropyltri($C_1$–$C_3$ alkyl)ammonium salts;
    (d) chlorohydroxypropyltri($C_1$–$C_3$ alkyl)ammonium salts; and
    (e) mixtures thereof;
  (ii) from about 1 to about 99.9% by weight of a cosmetically acceptable carrier; and
(B) instructions printed on or associated with the package indicating topical use of the composition on skin for purposes of controlling the signs of aging.

DETAILED DESCRIPTION OF THE INVENTION

Now it has been found that certain types of ammonium salts of polyols may control the signs of human skin aging. Three categories of quaternary ammonium salts are particularly useful to achieve objectives of the present invention. These are outlined below.

A first category of useful quaternary ammonium compounds are the salts of hydroxypropyltri($C_1$–$C_3$alkyl) ammonium mono-substituted monosaccharides. These can be prepared by a variety of procedures. Most preferred is via reaction of 2-hydroxy-3-chloropropyl trimethylammonium chloride with a mono-saccharide in an approximately 1:1 molar ratio in an alkaline medium. By typical Williamson synthesis, sodium chloride is eliminated thereby forming an ether linkage between the hydroxypropyl end of the quat and the mono-saccharide.

Mono-saccharides, particularly reducing and non-reducing cyclic mono-saccharides, are the smallest carbohydrate molecules encompassing the four-, five- and six-carbon sugars. Illustrative monosacchrides are ribose, deoxy ribose, glucose, fructose, arabinose, xylose, lyxose, allose, altrose, gulose, mannose, idose, galactose and talose. Most preferred are glucose and fructose as the mono-saccharide moiety which is to be substituted with the hydroxypropyltrimonium group.

Ordinarily the $C_1$–$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salts of this invention. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, glycolate, lactate, gluconate, and benzenesulfonate.

Particularly preferred quaternary ammonium salts of the first category are illustrated by structures I and II below, wherein $X^-$ is a halide. These formulas are intended as including all comformational isomers of the depicted structures.

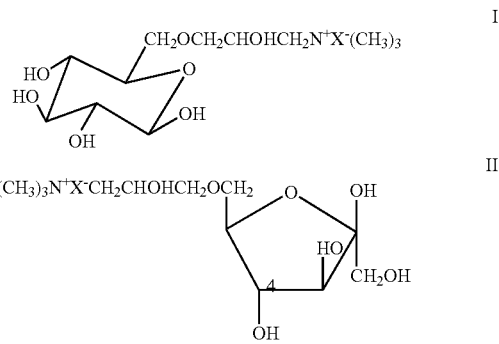

Advantageously compositions of the present invention will be formulated with a quaternary ammonium salt where the monosaccharide is only mono-substituted with hydroxypropyltri($C_1$–$C_3$ alkyl) ammonium groups. However, smaller amounts of di- and tri-substituted monosaccharide may also be present. These amounts normally may range from 0 to 20%, possibly from about 2 to about 10% by weight based on the weight of the quaternary ammonium compound present. More specifically, the multi-substituted mono-saccharide may be di-[hydroxypropyltri($C_1$–$C_3$ alkyl) ammonium]mono-saccharide, tri-[hydroxypropyltri($C_1$–$C_3$ alkyl) ammonium]mono-saccharide and mixtures thereof.

A second category of quaternary ammonium compound useful for this invention are the salts of hydroxypropyl tri($C_1$–$C_3$ alkyl) ammonium monosubstituted polyols. These can be formed in a variety of procedures. Most preferred is via reaction of 2-hydroxy-3-chloropropyl trimethyl ammonium chloride with a polyol, particularly a linear polyol in an approximately 1:1 molar ratio in an alkaline medium. By typical Williamson synthesis, sodium chloride is eliminated thereby forming an ether linkage between the hydroxypropyl end of the quat and the polyol. Typical polyols are sorbitol, pentaerythritol, neopentyl glycol, propylene glycol, dipropylene glycol and isoprene glycol.

The second category will comprise salts with a cation having an average molecular weight no higher than about 450, preferably no higher than about 400, and optimally between about 300 and 400. Further, the salt advantageously is liquid at 23° C. Thus, the $T_g$ preferably is no higher than about 10° C., more preferably no higher than about 0° C. The $T_g$ can be measured in a Differential Scanning Calorimeter.

A third category of suitable ammonium compounds are the hydroxypropyltri($C_1$–$C_3$ alkyl)ammonium salts. These salts may be obtained in a variety of synthetic procedures, most particularly by hydrolysis of chlorohydroxypropyltri ($C_1$–$C_3$ alkyl)ammonium salts. A most preferred species is 1,2-dihydroxypropyltrimonium chloride, wherein the $C_1$–$C_3$ alkyl is a methyl group. Also useful may be 2-hydroxy-3-chloropropyl trimethylammonium chloride.

Amounts of the quaternary ammonium compound may range from about 0.1 to about 30%, preferably from about 0.5 to about 20%, optimally from about 1% to about 12% by weight of the composition.

By the term personal care composition is meant any substance applied to a human body for improving appearance, cleansing, odor control or general aesthetics. Nonlimiting examples of personal care compositions include leave-on skin lotions and creams, shower gels, toilet bars, antiperspirants, deodorants, shave creams, depilatories, lipsticks, foundations, mascara, sunless tanners and sunscreen lotions.

Compositions of this invention will also include a cosmetically acceptable carrier. Amounts of the carrier may range from about 1 to about 99.9%, preferably from about 70 to about 95%, optimally from about 80 to about 90% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, natural or synthetic esters and hydrocarbons. Amounts of the emollients may range anywhere from about 0.1 to about 95%, preferably between about 1 and about 50% by weight of the composition.

Silicone oils may be divided into the volatile and non-volatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5\times10^{-6}$ to 0.1 $m^2$/s at 25° C. Among the preferred nonvolatile emollients useful in the present compositions are the polydimethyl siloxanes having viscosities from about $1\times10^{-5}$ to about $4\times10^{-4}$ $m^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

a) Alkyl esters of saturated fatty acids having 10 to 24 carbon atoms. Examples thereof include behenyl neopentanoate, isononyl isonanonoate, isopropyl myristate and octyl stearate.

b) Ether-esters such as fatty acid esters of ethoxylated saturated fatty alcohols.

c) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$–$C_{30}$ alcohols.

d) Wax esters such as beeswax, spermaceti wax and tribehenin wax.

e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$–$C_{13}$ isoparaffins, polybutenes and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Humectants may be employed in the present invention. These are generally polyhydric alcohol-type materials. Typical polyhydric alcohols include glycerol, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Personal care compositions of the present invention may be in any form. These forms may include lotions, creams, roll-on formulations, sticks, mousses, aerosol and non-aerosol sprays and fabric (e.g. nonwoven textile)-applied formulations such as via adhesive patches or via wipes.

Surfactants may also be present in compositions of the present invention. Total concentration of the surfactant when present may range from about 0.1 to about 90%, preferably from about 1 to about 40%, optimally from about 1 to about 20% by weight of the composition, and being highly dependent upon the type of personal care product. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Useful amphoteric surfactants include cocoamidopropyl betaine, $C_{12}$–$C_{20}$ trialkyl betaines, sodium lauroamphoacetate, and sodium laurodiamphoacetate.

Preferred anionic surfactants include soap, alkyl ether sulfates and sulfonates, alkyl sulfates and sulfonates, alkylbenzene sulfonates, alkyl and dialkyl sulfosuccinates, $C_8$–$C_{20}$ acyl isethionates, $C_8$–$C_{20}$ alkyl ether phosphates, $C_8$–$C_{20}$ sarcosinates, $C_8$–$C_{20}$ acyl lactylates, sulfoacetates and combinations thereof.

Sunscreen agents may also be included in compositions of the present invention. Particularly preferred are such materials as ethylhexyl p-methoxycinnamate, available as Parsol MCX®, Avobenzene, available as Parsol 1789® and benzophenone-3, also known as Oxybenzone. Inorganic sunscreen actives may be employed such as microfine (e.g. from 0.1 to 200 micron average size) titanium dioxide and zinc oxide. Amounts of the sunscreen agents when present may generally range from 0.1 to 30%, preferably from 2 to 20%, optimally from 4 to 10% by weight of the composition.

Antiperspirants and deodorant compositions of the present invention ordinarily will contain astringent actives. Examples include aluminum chloride, aluminum chlorhydrex, aluminim-zirconium chlorhydrex glycine, aluminum sulfate, zinc sulfate, zirconium and aluminum chlorohydroglycinate, zirconium hydroxychloride, zirconium and aluminum lactate, zinc phenolsulfonate and combinations thereof. Amounts of the astringents may range anywhere from about 0.5 to about 50% by weight of the composition.

Preservatives can desirably be incorporated into the personal care compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.0001% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Another type of useful substance can be that of an enzyme such as amylases, oxidases, proteases, lipases and combinations. Particularly preferred is superoxide dismutase, commercially available as Biocell SOD from the Brooks Company, USA.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from about 0.1 to about 10%, preferably from about 0.5 to about 2% by weight of the composition.

Desquamation promoters may be present. Illustrative are the alpha-hydroxycarboxylic acids and beta-hydroxycarboxylic acids. The term "acid" is meant to include not only the free acid but also salts and $C_1$–$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, aloe vera, grape seed, citrus unshui, willowbark, sage, thyme and rosemary.

Also included may be such materials as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

The compositions of the present invention can also be, optionally, incorporated into a water insoluble substrate for application to the skin such as in the form of a treated wipe.

A wide variety of packaging can be employed to store and deliver the personal care compositions. Packaging is often dependent upon the type of personal care end-use. For instance, leave-on skin lotions and creams and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film. All of the aforementioned are considered packaging within the context of the present invention.

The "signs of aging" according to the present invention means fine lines, wrinkles, hyperpigmentation, sagging skin, lack of radiance, dark under-eye circles, puffy eyes, sallowness, spider veins, appearance of cellulite and combinations thereof. These signs of aging according to the present invention can either be prevented from progressing, can be reduced or minimized through treatment with the compositions of the present invention.

Instructions on achieving treatment of the signs of aging can be provided as a writing directly on outer surfaces of packaging cartons, as instructional inserts within the package or other advertising associated with the packaged product.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

Herein is illustrated a lotion according to the present invention with a formula as outlined in Table I below. This formula is packaged in a standard polypropylene bottle with screw-top. A label around the outside of the bottle specifies that the composition has effectiveness against the signs of aging including removal of fine lines and wrinkles.

TABLE I

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| Chloride Salt of Hydroxypropyltrimonium Glucose | 1.00 |
| PHASE B | |
| Xanthan Gum | 0.20 |
| Natrosol ® 250HHR (ethyl cellulose) | 0.50 |
| Butylene Glycol | 3.00 |
| Glycerin | 2.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12–15 Alkyl Octanoate | 3.00 |
| PHASE D | |
| Vitamin A Palmitate | 0.10 |
| Bisabolol | 0.01 |
| Vitamin A Acetate | 0.01 |
| Fragrance | 0.03 |
| Retinol 50C | 0.02 |
| Conjugated Linoleic Acid | 0.50 |

EXAMPLE 2

A water-in-oil topical liquid make-up foundation according to invention is described in Table II below. This foundation is delivered via a glass screw-top capped bottle. The bottle is placed within an outer carton. Inside the carton is placed instructions for use including applying the foundation to the face to achieve improvements in the signs of aging including enhanced radiance.

TABLE II

| INGREDIENT | WEIGHT % |
|---|---|
| PHASE A | |
| Cyclomethicone | 9.25 |
| Oleyl Oleate | 2.00 |
| Dimethicone Copolyol | 20.00 |

TABLE II-continued

| INGREDIENT | WEIGHT % |
|---|---|
| PHASE B | |
| Talc | 3.38 |
| Pigment (Iron Oxides) | 10.51 |
| Spheron L-1500 (Silica) | 0.50 |
| PHASE C | |
| Synthetic Wax Durachem 0602 | 0.10 |
| Arachidyl Behenate | 0.30 |
| PHASE D | |
| Cyclomethicone | 1.00 |
| Trihydroxystearin | 0.30 |
| PHASE E | |
| Laureth-7 | 0.50 |
| Propyl Paraben | 0.25 |
| PHASE F | |
| Fragrance | 0.05 |
| PHASE G | |
| Water | balance |
| Chloride Salt of Hydroxypropyltrimonium Fructose | 3.00 |
| Methyl Paraben | 0.12 |
| Propylene Glycol | 8.00 |
| Niacinamide | 4.00 |
| Glycerin | 3.00 |
| Sodium Chloride | 2.00 |
| Sodium Dehydroacetate | 0.30 |

EXAMPLE 3

Illustrated herein is a skin cream incorporating a quat salt of the present invention. The cream is deposited in a wide-mouth jar with screw-cap top. Printed on the label of the jar are instructions that the cream will control the signs of aging such as hyperpigmentation and sagging skin.

TABLE III

| INGREDIENT | WEIGHT % |
|---|---|
| Glycerin | 6.93 |
| Niacinamide | 5.00 |
| 2,3-Dihydroxypropyltrimethylammonium Chloride | 5.00 |
| Permethyl 101A[1] | 3.00 |
| Sepigel 305[2] | 2.50 |
| Q2-1403[3] | 2.00 |
| Linseed Oil | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |
| Disodium EDTA | 0.10 |
| Glydant Plus[6] | 0.10 |
| PEG-100 Stearate | 0.10 |
| Stearic Acid | 0.10 |
| Purified Water | Balance |

[1]Isohexadecane, Presperse Inc., South Plainfield, NJ
[2]Polyacrylamide(and)C13–14 Isoparaffin(and) Laureth-7, Seppic Corporation, Fairfield, NJ
[3]dimethicone(and)dimethiconol, Dow Corning Corp. Midland, MI
[4]Sorbitan Monostearate and Sucrococoate, ICI Americas Inc., Wilmington, DE
[5]Sucrose ester of fatty acid
[6]DMDM Hydantoin (and) Iodopropynyl Butylcarbamate, Lonza Inc., Fairlawn, NJ

EXAMPLE 4

Illustrative of another cosmetic personal care composition incorporating a quat salt according to the present invention is the formula of Table IV. This composition is packaged in a plastic polypropylene tube with flexible side walls for pressing the composition through a tube orifice. Instructions are printed on the outside of the tube directing that the composition be applied to the face and that in a period from about 2 weeks to about 6 months, the signs of aging will have diminished.

TABLE IV

| INGREDIENT | WEIGHT % |
|---|---|
| Polysilicone-11 | 29 |
| Cyclomethicone | 59 |
| Petrolatum | 11 |
| Chloride Salt of Hydroxypropyltrimonium Sorbitol | 0.2 |
| Dimethicone Copolyol | 0.5 |
| Sunflowerseed Oil | 0.3 |

EXAMPLE 5

A relatively anhydrous composition incorporating a quat salt of the present invention is reported in Table V. This composition is packaged in a polyethylene squeezable tube and the tube placed within a folded carton. The carton includes instructions printed thereon for the consumer to apply the composition to the face. The instructions further indicate that the signs of aging will decrease by at least 20% over a 4 month period of usage.

TABLE V

| INGREDIENT | WEIGHT % |
|---|---|
| Cyclomethicone | 80.65 |
| Dimethicone | 9.60 |
| Squalane | 6.00 |
| Isostearic Acid | 1.90 |
| Borage Seed Oil | 0.90 |
| Chloride Salt of Hydroxypropyltrimonium Glucose | 0.50 |
| Retinyl Palmitate | 0.25 |
| Ceramide 6 | 0.10 |
| Tocopherol | 0.10 |

EXAMPLE 6

An aerosol packaged foaming cleanser with a quat salt suitable for the present invention is outlined in Table VI. Instructions on the method of using the cleanser will be printed on the plastic bottle serving as packaging for this aerosol dispensed product. The dispenser is available from the Airspray Corporation.

TABLE VI

| INGREDIENT | WEIGHT % |
|---|---|
| Sunflower Seed Oil | 20.00 |
| Maleated Soybean Oil | 5.00 |
| Silicone Urethane | 1.00 |
| Polyglycero-4 Oleate | 1.00 |
| Sodium C14–16 Olefin Sulfonate | 15.00 |
| Sodium Lauryl Ether Sulphate (25% active) | 15.00 |
| Cocoamidopropylbetaine | 15.00 |

TABLE VI-continued

| INGREDIENT | WEIGHT % |
| --- | --- |
| DC 1784 ® (Silicone Emulsion 50%) | 5.00 |
| Polyquaternium-11 | 1.00 |
| 2,3-Dihydroxypropyltriethylammonium Chloride | 1.00 |
| Water | Balance |

EXAMPLE 7

A disposable, single use personal care towelette product is described according to the present invention. A 70/30 polyester/rayon non-woven towelette is prepared with a weight of 1.8 grams and dimensions of 15 cm by 20 cm. Onto this towelette is impregnated a composition as outlined in Table VII below. The impregnated towelette is then packaged within a polypropylene foil. Printed on the outside of the foil are instructions for use. These include direction to apply the towelette over the face to achieve a reduction in the signs of aging including those of fine lines and wrinkles.

TABLE VII

| INGREDIENT | WEIGHT % |
| --- | --- |
| Chloride Salt of Hydroxypropyltrimonium Glucose | 7.50 |
| Glycerin | 2.00 |
| Hexylene Glycol | 2.00 |
| Disodium Capryl Amphodiacetate | 1.00 |
| Gluconolactone | 0.90 |
| Silicone Microemulsion | 0.85 |
| Witch Hazel | 0.50 |
| PEG-40 Hydrogenated Castor Oil | 0.50 |
| Fragrance | 0.20 |
| Vitamin E Acetate | 0.001 |
| Water | Balance |

EXAMPLE 8

A toilette bar illustrative of the present invention is outlined under Table VIII. The bar is placed within a folded cardboard carton. A foil is placed around the carton. Printing on the foil indicates that the bar should be used on face and body surfaces. Further, the label indicates that the bar composition will reduce signs of aging such as those of fine lines and wrinkles.

TABLE VIII

| INGREDIENT | WEIGHT % |
| --- | --- |
| Sodium Soap (85/15 Tallow/Coconut) | 77.77 |
| Chloride Salt of Hydroxypropyltrimonium Glucose | 3.50 |
| Glycerin | 2.50 |
| Sodium Chloride | 0.77 |
| Titanium Dioxide | 0.40 |
| Fragrance | 1.50 |
| Disodium EDTA | 0.02 |
| Sodium Etidronate | 0.02 |
| Fluorescer | 0.024 |
| Water | Balance |

EXAMPLE 9

This Example illustrates an antiperspirant/deodorant formula incorporating the anti-aging actives according to the present invention. The formula is placed within a propel-repel plastic container typical of antiperspirant/deodorant stick and soft-solid products. On the outside of the plastic package are instructions for applying the formula to the underarms to eliminate sagging skin.

TABLE IX

| Ingredient | Weight % |
| --- | --- |
| Cyclopentasiloxane | 44 |
| Dimethicone | 20 |
| Aluminum Zirconium Trichlorohydrex Glycinate | 15 |
| Chloride Salt of Hydroxypropyltrimonium Glucose | 5.0 |
| $C_{18}$–$C_{36}$ Acid Triglyceride | 5.0 |
| Microcrystalline Wax | 3.0 |
| Glycerin | 3.0 |
| Silica | 2.5 |
| Dimethicone Crosspolymer | 1.0 |
| Fragrance | 0.5 |
| Disodium EDTA | 0.4 |
| Butylated Hydroxytoluene | 0.3 |
| Citric Acid | 0.3 |

EXAMPLE 10

Anti-aging efficacy of representative quaternary ammonium polyol salts of this invention were evaluated in a Procollagen I Expression test.

Procedure for Measuring Procollagen-I Synthesis in Human Dermal Fibroblasts

Preparation of Dermal Fibroblast Conditioned Medium

Primary human foreskin fibroblasts (from a 55 year old donor) at passage 2 (P2) were seeded into 12-well plates at 10000 cells/cm$^2$ and maintained for 24 hours in an atmosphere of 5% carbon dioxide and 4% oxygen in Dulbeccos Modified Eagles Medium (DMEM) supplemented with 10% foetal calf serum. After this time the cells were washed with serum free DMEM and then incubated in fresh serum free DMEM for a further 60 hours. The fibroblast monolayers were then washed again with serum free DMEM. Test reagents and vehicle controls were added to the cells in triplicate in a final volume of 0.4 ml/well fresh serum free DMEM and incubated for a further 24 hours.

This fibroblast conditioned medium was either analyzed immediately or snap frozen in liquid nitrogen and stored at −70° C. for future analysis. The cells were then counted and data from the dot-blot analysis subsequently standardized to cell number.

Dot Blot Assay for Procollagen-I Protein in Dermal Fibroblast Conditioned Medium Samples of conditioned medium from dermal fibroblasts treated with vehicle (as a control) or test reagents were supplemented with 20 mM dithiothreitol (1:10 dilution of 200 mM stock solution) and 0.1% sodium dodecylsulphate (1:100 dilution of 10% stock solution), mixed well and then incubated at 75° C. for 2 minutes.

A standard for the assay was generated by serial dilution of neat fibroblast conditioned medium from fibroblasts seeded at 10000 cells/cm$^2$ in a 175 cm$^2$ flask and maintained in serum free DMEM as described above. Assay samples were subsequently applied in triplicate to a prewetted sheet of Immobilon-P transfer membrane using the 96-well Bio-Dot Apparatus from Bio-Rad as described in the manufacturers guidelines. Approximately 200 µl of medium was applied per well. The medium was allowed to filter through the membrane under gravity (30 minutes) after which the membrane was washed twice with PBS (200 µl). These PBS washes were allowed to filter through the membrane under gravity (2×15 minutes).

The Bio-Dot apparatus was then attached to a vacuum manifold and a third and final PBS wash carried out under suction. The apparatus was disassembled, the membrane removed and quickly cut as required before being placed in blocking buffer overnight at 4° C. Membranes prepared for procollagen-I analysis were blocked with 5% (w/v) non-fat dried milk powder/0.05% Tween 20 in PBS. The following day, the membranes were probed with 1:10000 dilution of primary antibodies to human procollagen-I (MAB1912; rat monoclonal; Chemicon Int. Inc., Temecula, Calif.) for 2 hours at room temperature. The membranes were subsequently washed with TBS/0.05% Tween 20 (3×5 minutes) and then incubated with 1:1000 dilution of $^{125}$I-conjugated anti-rat fragments (Amersham) as required for 1 hour at room temperature. Following this the Immobilon strips were again washed with TBS/Tween 20 (3×5 minutes) before being allowed to dry in air at room temperature.

The dried membranes were wrapped in cellophane and exposed to a Molecular Dynamics storage phosphor screen for 16–18 hours. At the end of this time the exposed screen was scanned by a phosphorimager (Molecular Dynamics Phosphorimager SF) using ImageQuant™ software. Dot intensity was assessed by computer-assisted image analysis using the quantification tools in ImageQuant™, standardized to cell number. The effects of various test reagents in procollagen-I synthesis were determined relative to a vehicle treated control value of 100 artibrary units. Results are recorded in Table X.

TABLE X

| Sample | Dosage (µM) | Procollagen protein (arbitrary units). Control set at 100% |
|---|---|---|
| Control | — | 100 |
| Choline | 100 | 103.1 |
| Compound A | 100 | 120.7 |
| Compound B | 100 | 139.2 |
| Compound C | 100 | 148.0 |
| Fructose/Glucose | 100 | 140.1 |
| Choline | 10 | 130.4 |
| Compound A | 10 | 122.1 |
| Compound B | 10 | 131.4 |
| Compound C | 10 | 144.2 |
| Fructose/Glucose | 10 | 150.8 |
| Choline | 1 | 169.2 |
| Compound A | 1 | 169.7 |
| Compound B | 1 | 150.3 |
| Compound C | 1 | 138.9 |
| Fructose/Glucose | 1 | 123.8 |

* Compound A: 2-hydroxy-3-chloropropyl trimethylammonium chloride Compound B: 2,3-dihydroxypropyltrimethylammonium chloride Compound C: 2-hydroxypropyltrimethylammonium chloride adduct of fructose/glucose All samples except choline at 100 µM concentration were statistically (P<0.05) significantly different from the control. Based on the results, it is evident that the quaternary ammonium polyols defined by the present invention respond positively in this test, which is indicative of anti-aging activity.

EXAMPLE 11

This Example details the synthesis of 2,3-dihydroxypropyl trimethylammonium chloride. A 125 ml erlenmeyer flask was charged with 16.7 ml (53 mmol) of 3-chloro-2-hydroxypropyl trimethylammonium chloride (employed as a 60% material in water as Quat 188®). The flask was equipped with a dropping funnel and stirring bar. A solution of sodium hydroxide (55 ml, 55.0 mmol) was charged into the flask via the dropping funnel at a rate to maintain room temperature of the reaction. Once addition was complete, the solution was stirred under ambient conditions for about 12 hours, followed by heating at 50° C. for two hours.

Progress of the reaction was monitored by thin layer chromatography (TLC). Product was spotted on a 2.5 by 7.6 cm silica gel plate alongside the starting material and eluted with butanol: acetic acid: water (4:222) for approximately 50 minutes. Visualization was executed with ninhydrin stain and scorching on a hotplate.

Crude product solution was first acidified to pH of 7, and then concentrated to remove water. Ethanol (200 ml) was added to the crude product with stirring. Upon sitting, sodium chloride precipitated and was filtered off under vacuum. The filtrate was concentrated under vacuum on a Rotavap®, followed by additional drying under high vacuum (0.05 mmHg). A cloudy gel was obtained yielding the final product in 97% yield. TLC analysis indicated a major spot at $R_f$=0.27.

A 60 MHz proton NMR ($D_2O$ w/TSP) was run on the final product. The spectra confirmed the final product structure. Mass Spectrum analysis in positive ion mode revealed a $M^+$ of 134 (minus chlorine).

EXAMPLE 12

This Example details the synthesis of glucose hydroxypropyl trimethylammonium chloride. A round bottom 250 ml flask was fitted with a mechanical stirrer. Into the flask was charged 1 M sodium hydroxide (55.5 ml, 55.5 mmol), Clearsweet 95 (10 g, 55.5 mmol) and 3-chloro-2-hydroxypropyl trimethylammonium chloride (15 ml, 55.5 mmol). Clearsweet 95 is a trademark of Cargill and contains 95.4% glucose, 2.8% maltose and 1.8% higher sugars. The 3-chloro-2-hydroxypropyl trimethylammonium chloride was sourced from Aldrich Chemical Company as a 60% active material in water. It is also available as Quat® 188 from the Dow Chemical Company. The reactants were stirred at room temperature for 18 hours. Water was removed under reduced pressure at 50° C. to give a heterogeneous colorless syrup. Filtration through glass wool afforded glucose hydroxypropyl trimethylammonium chloride as a homogeneous clear and colorless syrup: m/z (ESI; $M^+$–$Cl^-$) 296; HPLC (Column: YMC-ODS-AQ, S5, 120A, 4.6×250 mm; Flow: 1 ml/min isocratic, 100% water; Detector: RI; Temperature: 35° C.) $t_r$ 3.11 min (Clearsweet 95-$t_r$ 3.09 min; CHPTMAC-$t_r$ 3.39 min).

EXAMPLE 13

This Example details the synthesis of fructose hydroxypropyl trimethylammonium chloride. A round bottom 250 ml flask was fitted with a mechanical stirrer. Into the flask was charged 1 M sodium hydroxide (55.5 ml, 55.5 mmol), Cornsweet (10 g, 55.5 mmol) and 3-chloro-2-hydroxypropyl trimethylammonium chloride (15 ml, 55.5 mmol). Cornsweet is obtained from the Archer Daniels Midland Corporation as a 100% fructose material. The 3-chloro-2-hydroxypropyl trimethyl ammonium chloride was sourced from Aldrich Chemical Company as a 60% active material in water. It is also available as Quat® 188 from the Dow Chemical Company. The reactants were stirred at room temperature for 18 hours. Water was removed under reduced pressure at 50° C. to give a heterogeneous colorless syrup. Filtration through glass wool afforded fructose hydroxypropyl trimethylammonium chloride as a homogeneous clear and colorless syrup: m/z (ESI; $M^+$–$Cl^-$) 296; HPLC (Column: YMC-ODS-AQ, S5, 120A, 4.6×250 mm; Flow: 1 ml/min isocratic, 100% water; Detector: RI; Temperature: 35° C.) $t_r$ 3.16 min (Cornsweet-$t_r$ 3.17 min; CHPTMAC-$t_r$ 3.39 min).

EXAMPLE 14

Herein is described the preparation of a mixed fructose-glucose hydroxypropyl trimethylammonium chloride. A round bottom 250 ml flask was fitted with a mechanical stirrer. The flask was charged with 1 M sodium hydroxide (55.5 ml, 55.5 mmol) and a mixture of Clearsweet 95 (5 g, 27.8 mmol), Cornsweet (5 g, 27.8 mmol) and 3–chloro-2 hydroxypropyl trimethylammonium chloride (15 ml, 55.5 mmol). The solution was stirred at room temperature for 18 hours. Water was removed under reduced pressure at 50° C. resulting in a heterogeneous light yellow syrup. Filtration through glass wool afforded a mixture of glucose hydroxypropyl trimethylammonium chloride and fructose hydroxypropyl trimethylammonium chloride as a homogeneous clear light yellow syrup: m/z (ESI; $M^+$–$Cl^-$) 296; HPLC (Column: YMC-ODS-AQ, S5, 120A, 4.6×250 mm; Flow: 1 ml/min isocratic, 100% water; Detector: RI; Temperature: 35° C.) $t_r$ 3.14 min (Clearsweet 95-$t_r$ 3.09 min; Cornsweet-$t_r$ 3.17 min. CHPTMAC-$t_r$ 3.39 min).

EXAMPLE 15

Herein is provided a synthesis procedure for the chloride salt of hydroxypropyltrimonium sorbitol (also referred to as 'Sorbitol Monoquat'). A round bottom 250 ml flask was fitted with a mechanical stirrer. Into the flask was charged a mixture of sorbitol (10 g, 55.0 mmol) and 3-chloro-2-hydroxypropyl trimethylammonium chloride (Quat 188®) (15 ml, 55.0 mmol). One molar sodium hydroxide (55.0 ml, 55.0 mmol) was then added to the charged mixture. The resultant solution was stirred at room temperature for 18 hours. Water was then removed under reduced pressure at 50° C. yielding a heterogeneous colorless syrup. Filtration through glass wool afforded sorbitol hydroxypropyltrimethylammonium chloride as a homogeneous clear syrup: m/z (ESI; $M^+$–$Cl^-$) 298.

What is claimed is:

1. A method for treating signs of aging in human skin, the method comprising applying to the face and body surfaces a personal care composition comprising:
   (i) from about 0.1 to about 30% by weight of a quaternary ammonium compound selected from the group consisting of:
      (a) salts of hydroxypropyltri($C_1$–$C_3$ alkyl)ammonium mono-substituted polyols, the salts having a cation of an average molecular weight no higher than about 450 and the salts having a $T_g$ no higher than about 10° C.;
      (b) dihydroxypropyltri($C_1$–$C_3$ alkyl)ammonium salts;
      (c) chlorohydroxypropyltri($C_1$–$C_3$ alkyl)ammonium salts; and
      (d) mixtures thereof;
   (ii) from about 1 to about 99.9% by weight of a cosmetically acceptable carrier.

2. The method according to claim 1 wherein the personal care composition is selected from the group consisting of leave-on skin lotions and creams, shower gels, toilette bars, antiperspirants, deodorants, shave creams, depilatories, lipsticks, foundations, mascara, sunless tanner and sunscreen lotions.

3. The method according to claim 1 wherein the salt of (b) is dihydroxypropyl trimonium chloride.

4. The method according to claim 1 wherein the polyols are selected from the group consisting of sorbitol, pentaerythritol, neopentyl glycol, propylene glycol, dipropylene glycol and isoprene glycol.

5. The method according to claim 1 wherein the salts (a) are chlorides of hydroxypropyl trimonium sorbitol.

6. The method according to claim 1 wherein the signs of aging are selected from the group consisting of fine lines, wrinkles, sagging skin, lack of radiance, dark under-eye circles, puffy eyes, sallowness, spider veins, appearance of cellulite and combinations thereof.

7. The method according to claim 1 wherein the quaternary ammonium compound ranges from about 2 to about 10% by weight.

* * * * *